(12) United States Patent
Paradis et al.

(10) Patent No.: US 9,554,863 B2
(45) Date of Patent: Jan. 31, 2017

(54) HIP REPLACEMENT IN COMPUTER-ASSISTED SURGERY

(71) Applicant: ORTHOSOFT, INC., Montreal (CA)

(72) Inventors: Francois Paradis, Boucherville (CA); Louis-Philippe Amiot, Hampstead (CA); Daniel Odermatt, Fort Lauderdale, FL (US)

(73) Assignee: ORTHOSOFT INC., Montreal (CA)

( * ) Notice: Subject to any disclaimer, the term of this patent is extended or adjusted under 35 U.S.C. 154(b) by 218 days.

(21) Appl. No.: 14/303,099

(22) Filed: Jun. 12, 2014

(65) Prior Publication Data

US 2014/0296856 A1    Oct. 2, 2014

Related U.S. Application Data

(62) Division of application No. 12/249,393, filed on Oct. 10, 2008.

(60) Provisional application No. 60/978,875, filed on Oct. 10, 2007.

(51) Int. Cl.
*A61B 34/20* (2016.01)
*A61B 19/00* (2006.01)
*A61B 17/16* (2006.01)
*A61F 2/46* (2006.01)

(52) U.S. Cl.
CPC ....... *A61B 19/5244* (2013.01); *A61B 17/1666* (2013.01); *A61B 34/20* (2016.02); *A61F 2/4609* (2013.01); *A61B 34/10* (2016.02)

(58) Field of Classification Search
CPC .................................................... A61B 34/20
USPC .......... 606/81, 91, 99, 102; 623/22.11–23.38
See application file for complete search history.

(56) References Cited

U.S. PATENT DOCUMENTS

| 4,632,111 | A | 12/1986 | Roche |
| 5,507,833 | A | 4/1996 | Bohn |
| 5,995,738 | A | 11/1999 | DiGioia, III et al. |
| 7,004,972 | B2 | 2/2006 | Yoon |
| 2003/0176783 | A1 | 9/2003 | Hu |

(Continued)

FOREIGN PATENT DOCUMENTS

| WO | 02/02028 A1 | 1/2002 |
| WO | 2004/069041 | 8/2004 |

(Continued)

*Primary Examiner* — David Bates
*Assistant Examiner* — Olivia C Chang
(74) *Attorney, Agent, or Firm* — Norton Rose Fulbright Canada LLP

(57) ABSTRACT

A system for calculating a position and orientation of an acetabular cup in computer-assisted surgery comprises a first trackable reference secured to a pelvis, with a frame of reference being associated with the first trackable reference. A device is positionable between a femoral neck and the acetabulum of the pelvis in a known relation, the device having a second trackable reference. Sensors track the trackable references for position and orientation. A position/orientation calculator calculates a position and orientation of the frame of reference and of the device and for determining an orientation of the neck axis with respect to the frame of reference from the known relation at a desired position of the femur. An implant position/orientation calculator provides cup implanting information with respect to the orientation of said neck axis as a function of the tracking for position and orientation of at least the first trackable reference.

8 Claims, 3 Drawing Sheets

(56) References Cited

U.S. PATENT DOCUMENTS

| | | |
|---|---|---|
| 2004/0092944 A1* | 5/2004 | Penenberg .............. A61B 34/20 606/91 |
| 2004/0097952 A1 | 5/2004 | Sarin et al. |
| 2004/0143340 A1 | 7/2004 | Tuma et al. |
| 2005/0119561 A1 | 6/2005 | Kienzle, III |
| 2005/0148855 A1 | 7/2005 | Kienzle, III |
| 2005/0281465 A1 | 12/2005 | Marquart et al. |
| 2006/0287613 A1 | 12/2006 | Amiot et al. |
| 2007/0225731 A1 | 9/2007 | Couture et al. |
| 2008/0146969 A1 | 6/2008 | Kurtz |

FOREIGN PATENT DOCUMENTS

| | | |
|---|---|---|
| WO | 2006/079211 | 8/2006 |
| WO | 2007/147235 | 12/2007 |

* cited by examiner

US 9,554,863 B2

HIP REPLACEMENT IN COMPUTER-ASSISTED SURGERY

CROSS-REFERENCE TO RELATED APPLICATION

This is a divisional application of U.S. patent application Ser. No. 12/249,393 filed on Oct. 10, 2008, which claims priority on U.S. Provisional Patent Application No. 60/978,875, filed on Oct. 10, 2007.

FIELD OF THE APPLICATION

The present application relates to total hip-replacement surgery using computer-assisted surgery systems and, more particularly, to a device, system and method for effecting total hip-replacement surgery.

BACKGROUND OF THE ART

Computer-assisted surgery (CAS) systems assist surgeons in different types of surgery like neurosurgery, total hip replacement (THR) and total knee replacement (TKR). Each of these surgeries presents numerous methods following different sequences of steps.

In THR, the patient can be positioned on his/her back or on his/her side during the surgery. Also, the surgeon can start either by working on the femoral head or on the acetabulum. Surgeons commonly start a THR by firstly working on the acetabulum, and thus by resurfacing the acetabulum to insert an acetabular cup implant. In the event that the cup is installed prior to the femoral implant being implanted, there are a few difficulties if the cup is not properly installed at the first try. If it isn't properly installed, the surgeon may remove the cup and reposition it, which can prove difficult without damaging the bone of the pelvis. Alternatively, the surgeon may compensate for the misalignment when installing the femoral implant. If the femoral and acetabular cup implants are misaligned, there are greater risks of dislocation of the femur, or impingement between the femoral implant neck and the acetabular cup or the pelvis.

When compared to the femoral implant, there is a greater range of possible positions/orientations associated with the implanting of an acetabular cup. It would be desirable to provide a method for selecting an orientation of the acetabular cup once the femoral implant is implanted, to lessen the risk of misalignment.

SUMMARY OF THE APPLICATION

It is therefore an aim of the present application to provide a novel method for performing hip replacement surgery using a computer-assisted surgery system.

It is a further aim of the present application to provide a trackable hip-joint device to digitize a projected femoral neck axis.

It is a further aim of the present application to provide a novel computer-assisted surgery system to perform total hip replacement.

Therefore, in accordance with the present application, there is provided a device for digitizing a femoral neck axis of with respect to a pelvic frame of reference in computer-assisted surgery, comprising: trackable member trackable for position and orientation by a computer-assisted surgery system; a body connected to the trackable member, the body having an interface portion adapted to be releasably coupled to a neck of one of an implanted femoral implant and a provisional in a known relation, and a bone interface portion adapted to be positioned against a pelvis such that the body of the device interrelates the implanted femoral implant or provisional to the pelvis, the neck axis of the femoral implant or provisional being calculable thereat with respect to the pelvic frame of reference as a function of the known relation and of the position and orientation of the trackable member.

Further in accordance with the present application, there is provided a method of doing surgical treatment in computer-assisted surgery for guiding an operator in inserting a cup implant of a hip joint implant into an acetabulum, comprising: positioning a trackable reference on a pelvis, the trackable reference being trackable in space for position and orientation so as to define a frame of reference; inserting any one of a provisional and a femoral implant into a femur; digitizing a neck axis of the provisional or femoral implant with respect to the frame of reference; and inserting the cup implant into the acetabulum by obtaining cup implanting information with respect to the orientation of said neck axis as a function of the tracking for position and orientation of the trackable reference.

Still further in accordance with the present application, obtaining cup implanting information comprises tracking an orientation of reamer altering the acetabulum.

Still further in accordance with the present application, obtaining cup implanting information comprises tracking an orientation of the cup implant being implanted.

Still further in accordance with the present application, the method comprises reaming the acetabulum prior to digitizing the neck axis.

Still further in accordance with the present application, digitizing the neck axis comprises coupling the neck of the provisional or femoral implant and the acetabulum with a tracked device, and orienting the femur to a desired posture.

Still further in accordance with the present application, digitizing the neck axis comprises orienting the femur to a desired posture.

Still further in accordance with the present application, doing surgical treatment is performed on a bone model or a cadaver.

Still further in accordance with the present application, there is provided a system for calculating a position and orientation of an acetabular cup in computer-assisted surgery, comprising: a first trackable reference secured to a pelvis, with a frame of reference being associated with the first trackable reference; a device positionable between a femoral neck and the acetabulum of the pelvis in a known relation, the device having a second trackable reference; sensors for tracking the trackable references for position and orientation; a position/orientation calculator for calculating a position and orientation of the frame of reference and of the device and for determining an orientation of the neck axis with respect to the frame of reference from the known relation at a desired position of the femur; and an implant position/orientation calculator for providing cup implanting information with respect to the orientation of said neck axis as a function of the tracking for position and orientation of at least the first trackable reference.

Still further in accordance with the present application, the system comprises a reamer for reaming the acetabulum of the pelvis, the reamer having another trackable reference such that the cup implanting information is calculated as a function of the orientation of the reamer.

Still further in accordance with the present application, the system comprises another trackable reference removably connected to the acetabular cup such that the cup implanting information is calculated as a function of the orientation of the acetabular cup.

Still further in accordance with the present application, the device comprises a body connected to the second trackable reference, the body having an interface portion adapted to be releasably coupled to a neck of an implanted femoral implant or provisional in the known relation, and a bone interface portion adapted to be positioned into the acetabulum such that the body of the device interrelates the implanted femoral implant to the pelvis.

Still further in accordance with the present application, the cup implanting information comprises anteversion angle, offset angle, limb length discrepancy, range of motion data, visal displays of an axis with respect to a pelvic image.

Still further in accordance with the present application, the desired posture comprises the patient in a regular lying posture.

Still further in accordance with the present application, the position/orientation calculator comprises a model of the device, and the known relation comprises the model of the device.

Still further in accordance with the present application, the femoral neck is the femoral neck of any one of a femoral implant and provisional.

DESCRIPTION OF PREFERRED EMBODIMENTS

Figure 1:
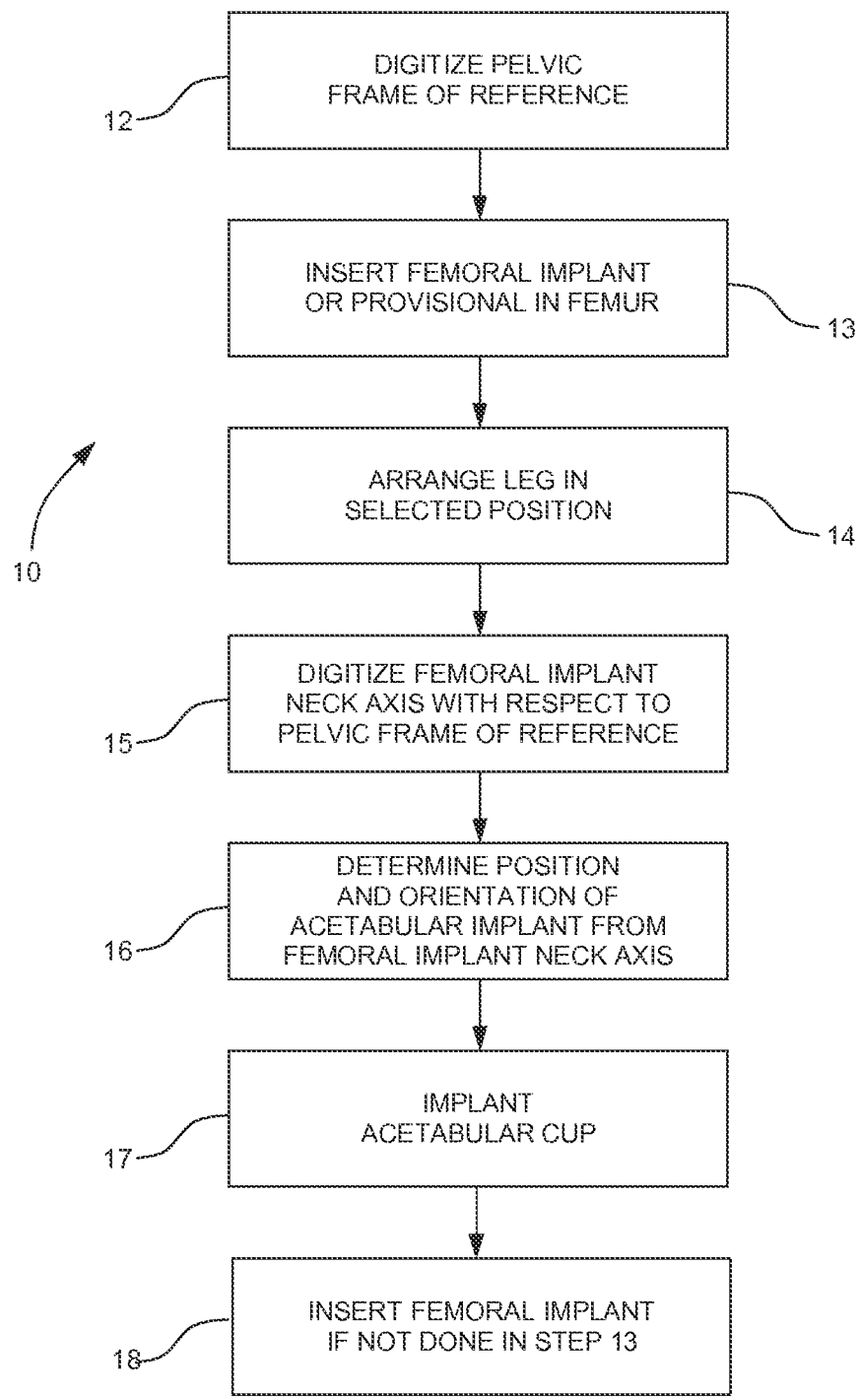
FIG. 1 is a flowchart illustrating a method for performing hip replacement using a CAS system in accordance with a first embodiment of the present application.

Referring to FIG. 1, a flowchart illustrating a method for performing hip replacement surgery in accordance with a first embodiment is generally shown at 10. The method 10 is for total hip replacement, namely, with the insertion of an acetabular cup in the acetabulum and of a femoral implant in the resected femur. The method 10 comprises the sequence of Steps 12 to 17.

Figure 3:
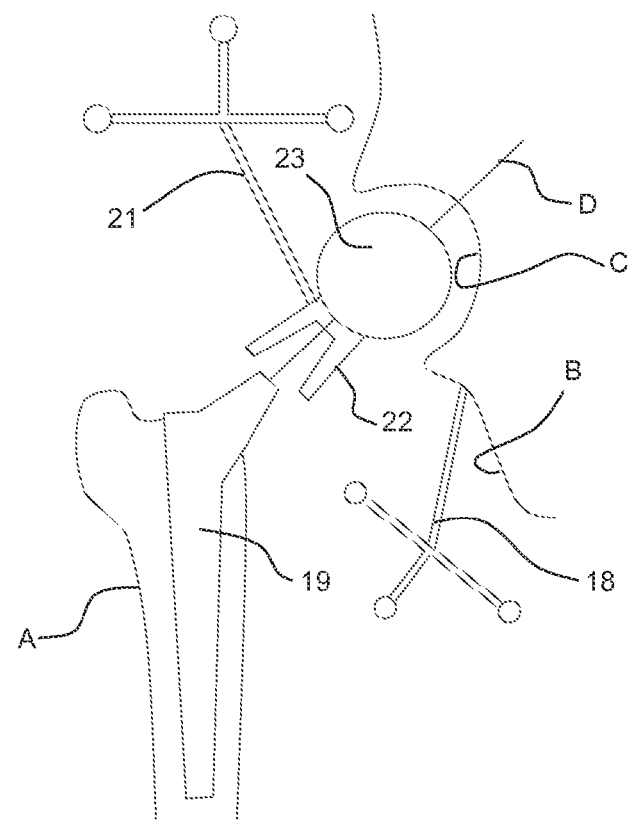
FIG. 3 is a schematic view of the trackable hip-joint device of FIG. 2 as used during hip-replacement surgery.

Referring to FIG. 3, the femur is schematically identified as A, as being positioned with respect to a pelvis B having an acetabulum C.

Referring to FIG. 1, in Step 12, a frame of reference is digitized for the pelvis. As an example, referring to FIG. 3, a trackable reference 18 is secured to the pelvis B, whereby a tracking of the trackable reference 18 provides position and orientation of points, forming a frame of reference. The frame of reference typically has a coordinate system with frontal, sagittal and transverse planes, and other information such as a 3D digitization of the acetabulum. In order to digitize the frame of reference, the hip joint is exposed by the surgeon.

Referring concurrently to FIGS. 1 and 3, in Step 13, the provisional or femoral implant 19 is inserted into the femur A. Step 13 may involve the resection of the femur A, the alteration (e.g., rasping) of the intramedullary canal of the femur A, and the positioning of the provisional or femoral implant 19 in the intramedullary canal. The provisional refers to any tool or device that is temporarily connected to the femur so as to simulate the position and orientation of the femoral implant 19 (e.g., the neck of the implant 19, a trial neck of a tool). For instance, the provisional is a rasp or like tool having a trial neck. For simplicity purposes, reference will now be made to the femoral implant 19, even though reference numeral 19 represents either a femoral implant or a provisional in FIG. 3.

In Step 14, the leg supporting the femoral implant 16 is positioned in a selected position in which the femur A and the pelvis B are in a desired postural relation. In an embodiment, the desired posture relation has the leg positioned approximately in the regular lying position of the patient (i.e., this selected position of the leg is used to take measurements such as anteversion and offset).

In Step 15, the femoral neck axis D is digitized with respect to the frame of reference of the pelvis (i.e., the trackable reference 18) at the desired postural relation. As will be described hereinafter, the digitization is performed by a trackable hip-joint device 20, although other alternatives are considered.

In Step 16, a desired position/orientation of the acetabular implant is determined from the femoral neck axis D digitized in Step 15. The desired position/orientation (i.e., cup implanting information) is selected to minimize the risk of dislocation, and maximize the range of movements of the provisional or femoral implant 19 with respect to the acetabular cup, in view of impingement.

In Step 17, the acetabular cup is implanted in the acetabulum C. This typically involves the reaming of the acetabulum C to an appropriate size, and the navigation of the acetabular cup to adjust the orientation of the cup in the reamed acetabulum C to have the cup implanted in the desired position/orientation as obtained in Step 16. It is pointed out that the reaming of the acetabulum C may optionally be performed prior to the resection of the femoral implant in Step 13.

Step 18 is performed if a provisional was used in Step 13. With the provisional removed, the femoral implant is inserted in its desired position.

Figure 2:
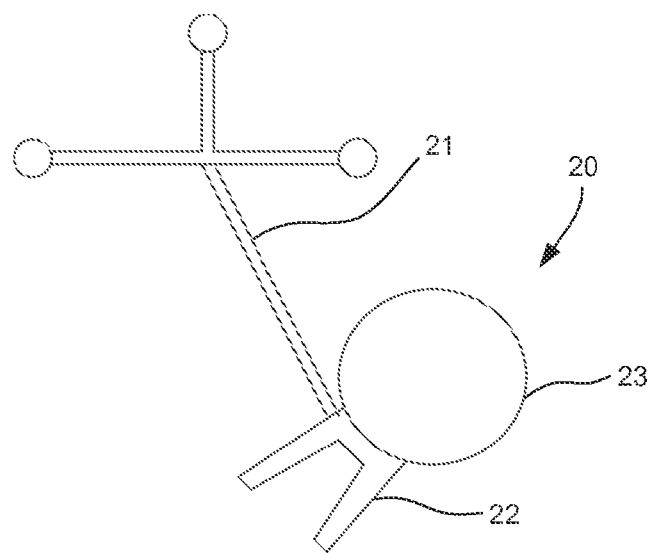
FIG. 2 is a schematic view of a trackable hip-joint device in accordance with a second embodiment of the present application.

In Step 15, it is desired to digitize the provisional or femoral implant neck D with respect to the pelvic frame of reference. Referring to FIG. 2, a trackable hip-joint device 20 is provided therefor. The trackable hip-joint device 20 has a trackable reference 21 that is tracked for position and orientation. The trackable reference 21 is connected to a body of the device 20, and more precisely to an implant interface 22. The implant interface 22 is shaped so as to connect to the neck of the provisional or femoral implant 19 in a known manner. A bone interface 23, embodied by a ball head, is connected to the implant interface 22. The bone interface 23 is shaped and selected as a function of the dimension of the acetabulum C.

In the embodiment of FIGS. 2 and 3, it is pointed out that both trackable references 18 and 21 are illustrated as being of the retro-reflective passive type (e.g., retro-reflective patterns such as spheres or circles in a known geometry), as used with an optical apparatus. However, other modes of tracking can be used, such as RF tracking, magnetic tracking, accelerometers, gyroscope, etc.

By way of a calibration or of a model provided by a CAS system, an axis D is provided along the implant interface 22 and the bone interface 23. As the implant interface 22 connects to the neck of the provisional or femoral implant 19 in a known manner, the axis is selected as being coincident with the axis D of the femoral neck of the femur A (with the implant 19).

Moreover, as the bone interface 23 is shaped as a ball head, it is selected in dimension as a function of the diameter of the acetabulum C, the interconnection between the femur and the pelvis is reproduced when the device 20 has its ball head accommodated in the acetabulum C and the interface 22 on the neck of the provisional or femoral implant 19. In an embodiment, the selected position of the leg described in Step 14 has the leg positioned preferably in full extension but can also be positioned with a certain degree of flexion, abduction/adduction or internal/external rotation to reproduce the position of the leg in the multiple functional positions representative of daily activities. Therefore, with the axis D being digitized at the selected position of the leg, the position/orientation data for the acetabular cup is used to calculate the optimal anteversion, inclination and offset whereby the range of motion of the implanted hip joint is calculable with respect to the pelvic frame of reference obtained in Step 12.

Alternative steps can be used to digitize the femoral neck axis as described in Step 15. For instance, it is considered to use a registration tool to digitize surface points on the neck of the implant 19 (FIG. 3) when the leg is in a full extension position.

It is observed that a reference anchored to the femur A can be used but is not needed. Therefore, the method 10 described above is not as invasive as other known CAS THR procedures. Moreover, some THR procedures require a trackable reference to be secured to the femur near the knee. Accordingly, trackable references often require additional incisions in the soft tissue, and these incisions are not required with the method 10 described above.

Figure 4:
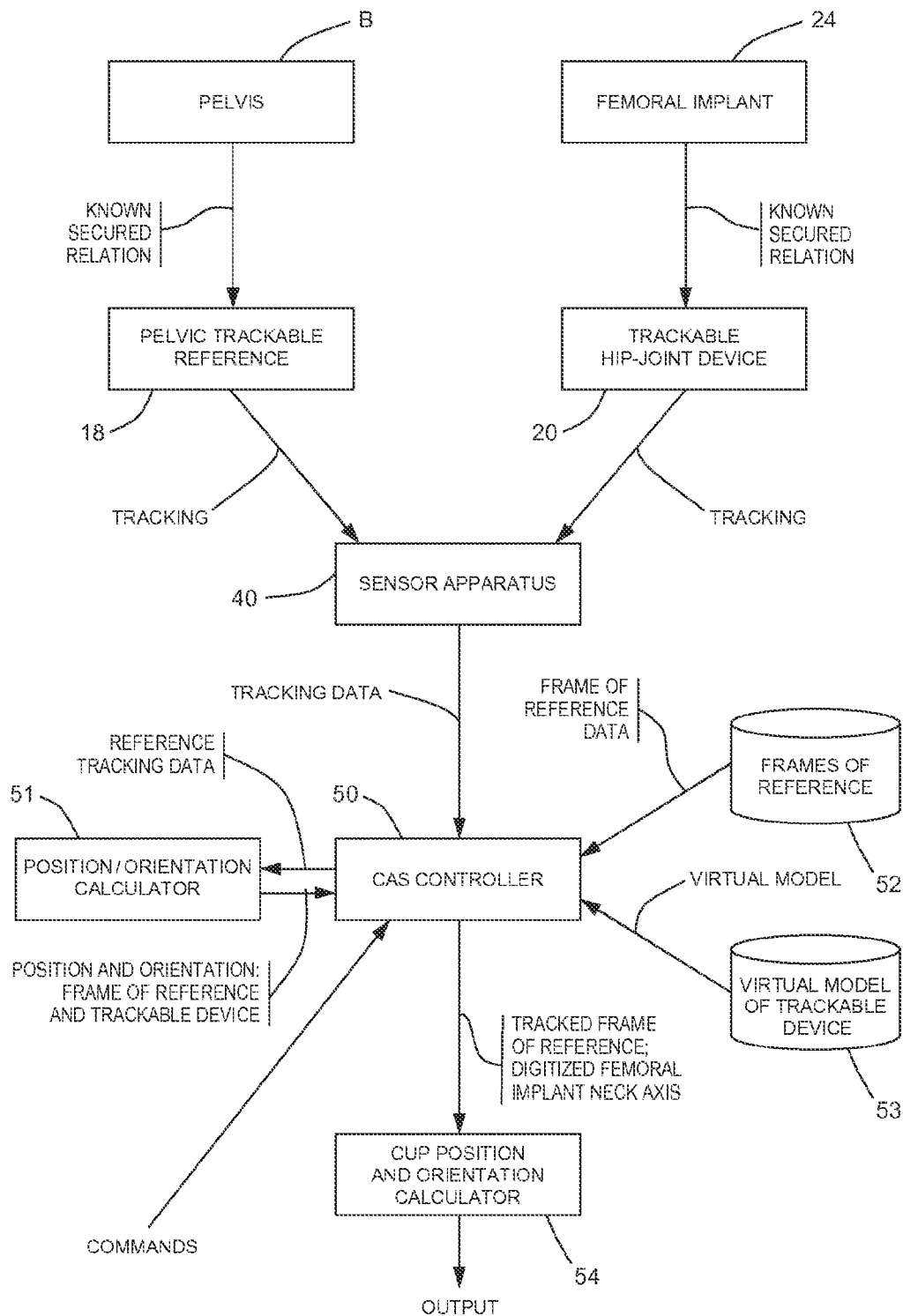
FIG. 4 is a block diagram illustrating a computer-assisted surgery system in accordance with another embodiment of the present application, for performing hip-replacement surgery.

Referring to FIG. 4, a computer-assisted surgery system used to perform THR, for instance using the method 10 described previously, is generally illustrated.

The computer-assisted surgery system has a sensor apparatus 40 that is provided to track the reference 18 and the device 20 in space for position and orientation. As mentioned previously, the sensor apparatus 40 may be any of an optical tracking apparatus, an RF tracking apparatus, and a magnetic tracking apparatus, accemelerometer/gyroscope systems.

The CAS system has a CAS controller 50. The controller 50 is a processing unit that receives commands from an operator and provides information to the surgeon through interfaces (i.e., screen, touchscreen, mouse, keyboard, etc.). The CAS controller 50 provides interactive information so as to guide the surgeon in the steps to follow throughout THR procedures.

A position/orientation calculator 51 is connected to the CAS controller 50. The calculator 51 provides position and orientation data pertaining to the pelvic frame of reference and to the trackable device 20 (i.e., position and orientation of the axis D). A database 52 is provided in conjunction with the CAS controller 50 so as to record digitization data related to the frame of reference. For instance, it may be desired to digitize a surface of the acetabulum C, to define planes (e.g., frontal, sagittal, transverse) for the frame of reference, or record the position and orientation of the femoral implant axis with regard to the pelvic frame of reference. Moreover, a calibration may be performed to obtain the axis D (FIG. 3) of the device 20. These types of information are typically recorded with the database 52.

Alternatively, a virtual model of the trackable device 20 may be provided by the database 53. In such a case, no calibration of the trackable device 20 is required. The operator identifies the selected trackable device 20 to the CAS controller 50, whereby the position of the axis D with respect to the trackable reference 21 is calculable by the position/orientation calculator 51 using the virtual model provided by the database 53.

A cup position and orientation calculator 54 is associated with the CAS controller 54 and determines a suitable position and orientation for the cup implant. The suitable position and orientation are calculated using the projected femoral neck axis as digitized with respect to the pelvic frame of reference. One contemplated way of providing the calculated cup implanting information is as surgical parameters, such as varying anteversion angle, offset angle, limb length discrepancy, as a function of the tracking of the cup implant. Alternatively, the information may be provided in the form of a range of motion of the hip joint.

The invention claimed is:

1. A system for calculating a position and orientation of an acetabular cup in computer-assisted surgery, comprising:
 a first trackable reference adapted to be secured to a pelvis, with a frame of reference being associated with the first trackable reference;
 a device adapted to be positioned between a femoral neck and an acetabulum of the pelvis to simultaneously physically loin the femoral neck to the acetabulum, the device having a second trackable reference;
 sensors for tracking the first and second trackable references;
 a position/orientation calculator for tracking the frame of reference of the first trackable reference, and for tracking the device, and for determining an orientation of a neck axis of the femoral neck with respect to the frame of reference when the device simultaneously physically loins the femoral neck to the acetabulum; and
 an implant position/orientation calculator for providing cup implanting information with respect to the orientation of said neck axis as a function of information provided by the sensors tracking at least the first trackable reference.

2. The system according to claim 1, further comprising a reamer for reaming the acetabulum of the pelvis, the reamer having another trackable reference such that the cup implanting information is calculated as a function of the orientation of the reamer.

3. The system according to claim 1, further comprising another trackable reference removably connectable to the acetabular cup such that the cup implanting information is calculated as a function of the orientation of the acetabular cup.

4. The system according to claim 1, wherein the device comprises a body connected to the second trackable reference, the body having an interface portion adapted to be releasably coupled to a neck of an implanted femoral implant or provisional, and a bone interface portion adapted to be positioned into the acetabulum such that the body of the device interrelates the implanted femoral implant to the pelvis when the device simultaneously physically joins the femoral neck to the acetabulum.

5. The system according to claim 1, wherein the cup implanting information comprises at least one of anteversion angle, offset angle, limb length discrepancy, range of motion data, visal displays of an axis with respect to a pelvic image.

6. The system according to claim 1, wherein the patient lies in a regular posture when the device simultaneously physically joins the femoral neck to the acetabulum.

7. The system according to claim 1, wherein the position/orientation calculator comprises a model of the device.

8. The system according to claim 1, wherein the femoral neck is the femoral neck of any one of a femoral implant and provisional.

\* \* \* \* \*